United States Patent [19]

Hooper

[11] Patent Number: 5,275,828
[45] Date of Patent: Jan. 4, 1994

[54] TREATMENT AND/OR A METHOD OF TREATING EQUINE VIRAL AND BACTERIAL INFECTIONS

[76] Inventor: Oswald E. Hooper, 1 Dunolly Place, Pukekohe, Auckland, New Zealand

[21] Appl. No.: 895,236

[22] Filed: Jun. 8, 1992

Related U.S. Application Data

[63] Continuation of Ser. No. 610,211, Nov. 8, 1990, abandoned.

[30] Foreign Application Priority Data

Nov. 8, 1989 [NZ] New Zealand .................. 231322
Jun. 7, 1990 [NZ] New Zealand .................. 233973

[51] Int. Cl.$^5$ .................. A61K 33/36; A61K 33/02; A61K 31/52
[52] U.S. Cl. .................. 424/670; 424/720; 514/263
[58] Field of Search .................. 424/670, 720; 514/263

[56] References Cited

U.S. PATENT DOCUMENTS

| | | | |
|---|---|---|---|
| 4,182,755 | 1/1980 | McNeff | 424/720 |
| 4,466,960 | 8/1984 | Silverman et al. | 514/263 |
| 4,743,591 | 5/1988 | Fukushima et al. | 514/30 |
| 4,904,472 | 2/1990 | Belardinelli et al. | 514/263 |

Primary Examiner—Frederick E. Waddell
Assistant Examiner—K. Weddington
Attorney, Agent, or Firm—Jacobson, Price, Holman & Stern

[57] ABSTRACT

The invention relates to a treatment for equine viral infections which includes potassium iodide, ammonium chloride and caffeine. A method of treating equine viral infections is also provided which involves administering the composition daily.

10 Claims, No Drawings

TREATMENT AND/OR A METHOD OF TREATING EQUINE VIRAL AND BACTERIAL INFECTIONS

This is a continuation of application Ser. No. 07/610,211, filed Nov. 8, 1990 which was abandoned upon the filing hereof.

This invention relates to a medicament and/or a method of treating viral infections and bacterial infections commonly associated therewith and has been developed particularly though not necessarily solely for use in the treatment of equine viral infections.

Horses are particularly prone to viral infections such as Herpes Virus Number 1. These viral infections are often present in association with bacterial infections. The symptoms include coughing and difficulty in breathing (probably a result of bronchitis), mucous formation, lethargy, weight loss, occasionally nose bleeding and pimples in the nostrils as well as weeping eyes.

The overall outcome of these infections is poor racing performance and overall appearance as well as lack of coat lustre.

In order to treat these infections, several veterinary preparations have been developed. However, most of these treatments only combat bacterial infections and therefore their usefulness is limited as they have no effect on viral infections. Bromoprimidine and Vendripulmin are commonly used to treat equine viral infections but these compounds appear to only exert their effect on bacterial infections.

BRIEF SUMMARY OF THE INVENTION

It is therefore an object of the present invention to provide a medicament and/or a method of treating viral infections and/or bacterial infections commonly associated therewith which will go at least someway to over the foreging desiderata or.

Accordingly in one aspect the invention consists in a medicament for treating viral and/or bacterial infections commonly associated therewith comprising a mixture of potassium iodide, ammonium chloride and caffeine.

In a further aspect the invention consists in a method of treating equine viral infections and/or bacterial infections commonly associated therewith comprising the steps of administering a medicament comprising a mixture of potassium iodide, ammonium chloride and caffeine to a patient.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

One preferred form of the invention will now be described.

In the preferred form of the invention a medicament and a method of treating viral infections and/or bacterial infections commonly associated therewith in particular equine viral infections are provided. However, the treatment can be used to treat humans and other animals such as cats, dogs and calves. Further, the treatment was found to have further applications such as blooming a healthy horse and may exert an inhibitory effect on bacterial infections which are commonly associated with viral infections.

A mixture is provided which includes potassium iodide, ammonium chloride and caffeine. Desirably, the mixture also includes aqueous chloroform and the mixture is provided in a suitable liquid carrier material such as water, for example.

The potassium iodide is desirably present in an amount between substantially 200 mg/L and substantially 800 mg/L.

The ammonium chloride is preferably present in amounts between substantially 200 mg/L and substantially 800 mg/L.

The caffeine is desirably present in amounts between substantially 200 mg/L and substantially 800 mg/L.

Aqueous chloroform is desirably provided as the chloroform acts as a preservative. The aqueous chloroform may for example be present in amounts in the desired quantity of between 10 ml/L and substantially 40 ml/L.

However, any one skilled in the art will appreciate that any other suitable preservative may be used and further compounds can be included in the composition if desired.

The mixture is used to treat equine viral infections by administering to a horse between substantially 30 ml and substantially 120 ml of the mixture on a daily basis. However, if the treatment is to be administered to an animal other than a horse the amount of mixture administered can be varied according to the body weight of the animal. The mixture is preferably administered orally but alternative administration means are envisaged by the applicant.

The preferred dosage rate is about 60 ml per day and the upper and lower limits are set because too great a quantity may have a toxicity which is too great for the animal whereas, of course, too low a quantity will reduce the efficacy of the mixture.

It is found that the mixture tends to act as a bronchodilator and also tends to dry up the mucus whilst acting as an expectorant.

The inventor has administered the medicament daily to over 200 horses suffering from what was diagnosed to be viral infections and experienced a 90% success rate in obviating the symptoms. The various symptoms displayed by the horses tested prior to treatment were coughing, wheezing, mucous formation, lethargy and ocassional nose bleeding and spot or pimple formation in the nose. These symptoms obviously effected the horse's racing performance and overall appearance. After treatment with the mixture disclosed herein it was found that, in most instances, the symptoms were no longer displayed by the horses after a period of about 14 days and many of the horses treated won races after the treatment. The daily dosage rate was 60 ml per day. When using the treatment it was found that in order to avoid recurrences of the symptoms the horse should not be "stressed" too soon after treatment.

The applicant has prepared several working sheets which clearly detail the effectiveness of the mixture for combatting the symptoms thought to be associated with viral infections. Many of these sheets have been signed by veterinarians witnessing the effectiveness of the composition. Several horses had been treated for up to two years with known drugs such as Bromoprimidine and Ventripulmin showing little improvement. However, treatment with the composition of the instant invention obviated the symptoms displayed by these horses.

The inventor has also administered the composition to healthy horses and it was found that the sheen of the horse's coat was improved. This was found to occur in unhealthy animals as well. Further, the treatment appeared to cure staggers. The inventor has also administered the composition to several cats and dogs and calves which appeared to be suffering from viral infections and an overall clearing of the symptoms was observed.

Not wishing to be bound by any theory it is hypothesised that the method by which the mixture effects its result is possibly due to the fact that the salts contained in the mixture are either salts of a strong base and a weak acid or a weak base and a strong acid. The applicant also believes that in solution complexes are formed which are only weakly soluble thereby giving a slow release of the materials.

It is believed that it will be found that administration of the above mixtures to horses in substantially the amounts shown will give substantial relief to those horses suffering from equine viral infections.

Thus it can be seen that a medicament and method of treating viral infections and/or bacterial infections commonly associated therewith is provided which will give relief, in particular, to horses having equine viral infections and it is found that the mixture gives greater relief than other presently known treatments such as antibiotics.

What is claimed is:

1. A medicament comprising an effective amount of a mixture of potassium iodide, ammonium chloride and caffeine for treating viral infections and bacterial infections commonly associated therewith.

2. A medicament comprising an effective amount of a mixture of potassium iodide, ammonium chloride and caffeine for treating equine viral infections and bacterial infections commonly associated therewith.

3. The medicament as claimed in claim 1 further comprising aqueous chloroform.

4. The medicament as claimed in claim 1 wherein said mixture comprises between about 200 mg/L and about 800 mg/L potassium iodide, between about 200 mg/L and about 800 mg/L ammonium chloride, and between about 200 mg/L and about 800 mg/L caffeine.

5. The medicament as claimed in claim 3 wherein said chloroform is provided in an amount between about 10 ml/L and about 40 ml/L.

6. A method of treating equine viral infections and bacterial infections commonly associated therewith comprising the step of administering a medicament comprising an effective amount of a mixture of potassium iodide, ammonium chloride and caffeine to a horse suffering from a viral infection.

7. The method of treating viral infections and bacterial infections commonly associated therewith as claimed in claim 6 wherein said mixture comprises between about 200 mg/L and about 800 mg/L potassium iodide, between about 200 mg/L and about 800 mg/L ammonium chloride, and between about 200 mg/L and about 800 mg/L caffeine, and the medicament is administered in the amount between about 30 ml and 120 ml on a daily basis.

8. The method of treating viral infections and bacterial infections commonly associated therewith as claimed in claim 6 wherein the medicament further comprises between about 10 ml/L and about 40 ml/L aqueous chloroform and the medicament is administered in an amount between about 30 ml and 120 ml on a daily basis.

9. The method of treating viral infections and bacterial infections commonly associated therewith as claimed in claim 6 wherein the medicament is administered in the amount of about 60 ml on a daily basis.

10. The method of treating viral infections and bacterial infections commonly associated therewith as claimed in claim 7 wherein the medicament is administered in the amount of about 60 ml on a daily basis.

* * * * *